United States Patent [19]

DuRoss

[11] Patent Number: 5,158,789
[45] Date of Patent: Oct. 27, 1992

[54] MELT COCRYSTALLIZED SORBITOL/XYLITOL COMPOSITIONS

[75] Inventor: James W. DuRoss, Smryna, Del.

[73] Assignee: ICI Americas Inc., Wilmington, Del.

[21] Appl. No.: 742,966

[22] Filed: Aug. 9, 1991

[51] Int. Cl.$^5$ .......................... A23G 3/30; A23L 1/22; A23L 1/09

[52] U.S. Cl. ........................................ 426/3; 426/658; 426/660; 426/453; 426/804

[58] Field of Search ............... 426/658, 660, 572, 661, 426/804, 3–6, 453

[56] References Cited

U.S. PATENT DOCUMENTS

| | | | |
|---|---|---|---|
| 3,558,725 | 1/1971 | Kohno et al. | 260/635 |
| 3,985,815 | 10/1976 | Jaffe et al. | 260/637 |
| 4,372,942 | 2/1983 | Cimiluca | 426/658 |
| 4,789,559 | 12/1988 | Hirao et al. | 426/658 |
| 5,023,092 | 6/1991 | DuRoss | 426/658 |
| 5,045,340 | 9/1991 | Kohler | 426/804 |

OTHER PUBLICATIONS

Kirk-Othmer, "Encyclopedia of Chemical Technology", vol. 1, pp. 765–772, John Wiley & Sons (1978).

*Primary Examiner*—Jeanette Hunter
*Attorney, Agent, or Firm*—William E. Dickheiser; Paul L. Sharer

[57] ABSTRACT

Melt cocrystallized sorbitol/xylitol offers improved processing properties relative to blends of crystalline sorbitol and crystalline xylitol. Also disclosed are ingestible compositions, such as tablets and chewing gum, comprising melt cocrystallized sorbitol/xylitol as well as a process for the production thereof.

8 Claims, No Drawings

MELT COCRYSTALLIZED SORBITOL/XYLITOL COMPOSITIONS

FIELD OF THE INVENTION

This invention relates to melt cocrystallized sorbitol/xylitol compositions which exhibit unexpectedly superior processing capabilities relative to blends produced by mixing equivalent amounts of melt crystallized sorbitol with melt crystallized xylitol. As such cocrystallized material may be more readily tableted and compounded into chewing gum, such materials may be more readily employed in confectionary and/or pharmaceutical compositions to take advantage of the cariogenic properties and other beneficial effects attributable to xylitol.

BACKGROUND OF THE INVENTION

Several research studies have shown that xylitol added to a cariogenic diet may reduce the caries incidence in man. Thus, for example, Wales et al, "The Effect of Xylitol on Plaque Metabolism", Swed. Dent. J., Volume 8, Issue 3, pp. 155–61 (1984) present evidence that Strep mitior and Strep mutans are unable to metabolize xylitol and transfer it to xylitol phosphate. Such article suggests that the accumulation of xylitol phosphate inside cells may poison bacteria and this possibly explains the cariestherapeutic effect of xylitol observed in some laboratories.

However, the incorporation of xylitol into pharmaceutical and/or confectionery products such as gum or tablets has been difficult due to the physical form of the aqueous crystallized xylitol available.

Thus, traditionally xylitol has been produced by the crystallization of a saturated aqueous solution of xylitol to form single crystals, tetrahedron in shape, of relatively uniform size. These crystals are grown in solution, separated from solution by centrifuging, drying the crystals and then grinding them into a powder. Thus, for example, Kirk-Othmer, Encyclopedia of Chemical Technology, Third Ed., (1978), John Wiley & Sons, indicate (at Vol. I, page 766) that "Xylose is obtained from sulfite liquors, particularly from hardwoods, such as birch, by methanol extraction of concentrates or dried sulfite lyes, ultrafiltration and reverse osmosis, ion exchange, ion exclusion, or combinations of these treatments . . . hydrogenation of xylose to xylitol is carried out in aqueous solution, usually at basic pH, with Raney nickel catalyst at a loading of 2%, at 125° C. and 3.5 MPa (515 psi)". An alternative aqueous crystallization process is described in U.S. Pat. No. 3,985,515 to Jaffe et al.

Xylitol produced in this fashion is typically very moisture sensitive and is thus prone to caking, making it difficult to use such product after periods of storage due to the clumping that typically occurs. When xylitol powder is employed in sucrose free chewing gum, where it is used as part of the sweetner/bulking agent as a replacement for sugar, manufacturers may typically bring in xylitol crystallized from solution in bulk, unground form then grind it down themselves, just prior to addition to the gum batch, in order to minimize caking and the problems associated therewith.

Moreover, due to its crystalline structure, i.e., distinct single crystal, definitive form, and very dense nature, when added to gum, aqueous crystallized xylitol does not "dry" the gum out and even with reductions in plasticizer, the gum is typically very soft and difficult to handle/process in gum plants. At the typical use levels of 7–15% (based on total weight), gum containing aqueous crystallized xylitol poses unique handling problems.

A further result of the single crystalline form of aqueous crystallized xylitol is that such structure does not allow for any "copenetration" of the crystals to effect a bond of the crystals; the dense nature of the crystal has very low plastic deformation characteristics or values and the bonding energy of the crystal is low. As a result, it is not possible to make a direct compression tablet from xylitol powder produced from an aqueous crystallization process. Rather, one must first "agglomerate" the xylitol powder by wetting it with water in a high velocity air stream to form an agglomerate, and then drying and sizing the resulting product. Product produced by this process can be used in direct compression applications to make tablets of good hardness and durability. It is an added expense however to have to agglomerate the product from the ground aqueous crystallized xylitol. The added expense plus the "grittiness" that is acquired in the agglomeration process has greatly limited the use of xylitol as an excipient for tablet manufacture.

My copending U.S. patent application Ser. No. 07/441,131 discloses pharmaceutical compositions comprising a sugar alcohol derived from at least one mono- or polysaccharide having dispersed within its crystal matrix particles of at least one pharmaceutically active compound, as well as a method of producing such a uniformly dispersed pharmaceutical composition. It has now been unexpectedly found that when sorbitol is employed as the saccharide derivative and xylitol as the dispersed pharmaceutical active, cocrystallized materials are produced which provide unexpectedly desirable processing activity relative to blends of the crystalline materials alone in the formation of consumables such as tablets, chewing gums, and the like.

SUMMARY OF THE INVENTION

In one aspect, the present invention is directed to melt cocrystallized sorbitol/xylitol.

In another aspect, the present invention is directed to an ingestable composition comprising melt crystallized sorbitol/xylitol.

In yet another aspect, the present invention is directed to a method of producing melt crystallized sorbitol/xylitol, which method comprises the steps of:

a) forming a homogeneous molten blend of sorbitol and xylitol;

b) cooling said homogeneous molten mixture under agitation until a viscous mass is formed; and c) cooling said mass slowly until the sorbitol/xylitol blend becomes fully crystallized.

DESCRIPTION OF THE PREFERRED EMBODIMENTS

The present invention is directed to melt cocrystallized sorbitol/xylitol, ingestable compositions comprising melt cocrystallized sorbitol/xylitol, and a process for making such a cocrystallized sugar alcohol product.

The weight ratio of sorbitol to xylitol contained in such composition may vary greatly, ranging from 99:1 to 1:99 by weight.

Preferably, however, for most ingestable compositions such as tablets, chewing gums and the like, the weight ratio of sorbitol to xylitol will range from between about 50:50 to about 97:3, most preferably from about 65:35 to about 95:5.

In general, the melt cocrystallized material of this invention will exhibit melting points several degrees lower, typically of from 88°-93° C. depending upon the sorbitol to xylitol ratio, than of melt crystallized sorbitol (about 99.3°) or of melt crystallized xylitol (about 96° C.). The heats of fusion of such material are slightly depressed from that of melt crystalline sorbitol at lower xylitol loadings (e.g., of up to about 20 weight percent) but tend to be intermediate to those of melt crystallized sorbitol (of about 36-37 cal/gm) and of melt crystallized xylitol (of about 51-52 cal/gm) alone.

One interesting phenomenon which has been noted is that the X-ray diffraction patterns of the cocrystallized material tends to more closely resemble that of melt crystallized xylitol (as opposed to that of melt crystallized sorbitol) at xylitol concentrations as low as 15 weight percent.

The melt cocrystallized sorbitol/xylitol of this invention may be produced by:

a) forming a homogeneous molten blend of sorbitol and xylitol;

b) cooling such homogeneous molten mixture under agitation until a viscous mass is formed; and c) cooling said mass slowly until the sorbitol/xylitol blend becomes fully crystalline.

Prior to forming the homogeneous blend of step A, the sugar alcohols employed herein generally are dried such that they have a water content of less than about 3 percent by weight. Preferably such water content is less than about 1 percent, and most preferably is less than about 0.5 percent by weight. The sugar alcohol starting materials may be dried to the desired water content by conventional means such as a continuous thin film evaporator or a batch vacuum cooker.

The dried molten xylitol and sorbitol are then typically blended in the desired ratios at temperatures in excess of their melting points, typically in the range from about 140° to about 190° C., employing conventional liquid blending techniques. Care must be taken, however, to ensure that agitation continues at the elevated temperature of the molten alcohol until complete dissolution or melting and thorough dispersion of the active compound in the molten sugar alcohol has occurred.

Once the molten xylitol and molten sorbitol have been uniformly dispersed, the temperature of the molten blend is then reduced while agitation continues. Such cooling with agitation results in the onset of crystallization. Agitation should be continued until the formulation becomes a viscous mass. By the term "viscous mass" is meant a composition which has a semi-solid, dough-like appearance; is extrudable; and is not liquid and runny. Typically, at this point the sugar alcohol is generally at least about 40 percent crystalline by weight. However, where high loadings of xylitol are present, a viscous mass may be present where as little as only 20 weight percent of the sugar alcohol blend has crystallized. If desired, the dispersion may be periodically monitored, e.g., by differential scanning calorimetry, until the required percentage crystallinity (which percentage can easily be determined by running trials at various times until a suitable viscous mass is formed and then determining the crystallinity of such viscous mass, e.g., by differential scanning calorimetry) is observed.

The viscous mass is removed from the agitating means and allowed to further cool until a solid crystalline mass. Although the mixture can be fully crystallized under agitation, this is generally not preferred as such solid material may block up the reactor and even damage the agitation means employed.

The fully crystalline mass may be ground, employing conventional grinding equipment, to provide a powder which can be formed into tablets or blended with additional excipients and formulated into chewing gums, tablets, and the like.

Large scale preparations may preferably be made employing a process wherein the molten xylitol is heated to a temperature of between about 140° C. and about 190° C. and subjected to agitation in a heated tank. The reaction mass is metered into a continuous twin shaft mixer of the intermeshing type. Mixers of this type are discussed in "Chemical Engineers Handbook", 5th Edition, edited by R. H. Petty and C. H. Chilton (1973) pages 19-21. Characteristics of these mixers are that they include intermeshing kneader blades mounted onto parallel shafts which rotate in the same direction and the same speed with close blade-to-wall and blade-to-blade clearances.

A preferred continuous mixer is the high shear Readco Continuous Processor made by Teledyne Readco of York, Pennsylvania. The mixer shown U.S. Pat. No. 2,419,250 and in U.S. Pat. No. 3,618,902 (both assigned to Teledyne, Inc.) can be used without modification; however, the cocrystallized sugar alcohol which is formed in the present process is much more easily handled if the mixer is equipped with an extrusion nozzle or plate. Other high shear continuous twin screw mixers which impart a high shearing force at low shaft speed to the material being processed can also be used. Such mixers include the Baker, Perkins Multi-Purpose (M-P) mixer made by Baker, Perkins, Inc., of Saginaw, Michigan, and the ZSK Twin Screw Compounding Extruder made by Werner and Pfleiderer Corporation of Stuttgart, Germany. The Baker, Perkins mixer is shown in U.S. Pat. Nos. 3,195,868 and 3,198,491. Alternative blade configurations can be used in mixers of this type are shown in U.S. Pat. Nos. 3,423,074 (assigned to Baker, Perkins) and 3,490,750 (assigned to Teledyne, Inc.). These mixers are available in various diameters and horse power ratings depending on the throughput required.

Preferably, a Readco Continuous Processor with kneader blade diameters of 5, 15, or 24 inches with feed and/or discharge screws is utilized. Further, the discharge nozzles are preferably provided with heating means in order that the surface of the partially solidified cylindrical ribbon of exiting magma does not prematurely crystallize ensuring a smooth discharge. Thus, one process for producing the cocrystallized compositions of this invention involves continuously introducing a feed comprising the molten magma into an elongated mixing zone having shaft means and a plurality of kneader blades mounted on the shaft means, the configuration of the kneader blades being such as to provide restricted clearances between the blades and the adjacent walls; simultaneously cooling and kneading the molten alcohol magma as it passes through the mixing zone until a viscous mass of molten sugar alcohol is obtained; and continuously discharging the blend from the mixing zone through an extrusion orifice and further cooling the blend to ambient temperature forming the melt cocrystallized sugar alcohol composition.

In carrying out the crystallization, the molten xylitol is preferably held in an agitated feed tank in a relatively dry atmosphere to inhibit moisture pickup such that the moisture content does not exceed about 1% by weight. In the operation of the mixing equipment, the feed rate and other operating parameters are adjusted such that as the cooling mass pass through the mixer, a molten blend having increased concentrations of crystals is generated as the magma passes through from the fed to the discharge orifice. The rotating screws move the molten magma from the center of the equipment to the outer cooled edge whereupon crystals are precipitated which act as a crystallizing seed for the remaining molten sugar alcohol. As the temperature profile drops from molten feed temperature to discharge temperature, the viscosity of melt increases due to the formation of the crystals. The action of the rotating screws pushes the crystallizing molten magma in the form of extrudate through the discharge orifice whereupon it is extruded as an elongated mass. The extrudate may then be conveniently cut into desired lengths and permitted to cool until crystallization is complete.

Care should be taken to ensure that the temperature of the emitted extrudate is not too hot, as the molten mass will not crystallize sufficiently and will therefore lose its shape. Not only is such material difficult to handle, but the product obtained may be an undesirable mixture of crystals and amorphous sugar alcohol glass. The problem can be corrected by decreasing the throughput time or jacket cooling temperature and other variables such as feed temperature, rotation speed, back pressure, etc. Under ideal operating conditions, the extrudate crystalline paste develops a solid outer shell of crystalline product which is only slightly wetter on the interior side with molten material. The hot extrudate when permitted to stand will fully crystallize, typically over a period of between about 6 hours or less and about 96 hours or more depending on the cross-sectional dimension of the extrudate mass (which typically ranges in cross-sectional from about 5 to about 20 millimeters). Longer periods may be required for extruded shapes having a cross-sectional dimension of greater than 20 millimeters.

The melt crystallized and ground sorbitol/xylitol may be formulated into ingestable compositions employing conventional techniques and ingredients well known to those or ordinary skill in the art. As is shown in the Examples below, the use of the cocrystallized material provides unexpectedly superior processing advantages, such as reduced grittiness in tablets and reduced stickiness in gum formulations, relative to compositions employing equalent ratios of blended crystallized sorbitol with blended crystalline xylitol.

EXAMPLES

The following Examples are intended to further illustrate the invention and are not intended to limit the scope of the invention in any matter whatsoever. In such Examples, all proportions expressed are by weight unless otherwise specified.

EXAMPLES 1-5 AND COMPARATIVE EXPERIMENTS A AND B

Employing a laboratory size Readco mixer having counter-rotating mixing blades 2 inches in diameter and a barrel length of 18 inches, several batches of melt cocrystallized sorbitol/xylitol (Examples 1-5) having varying weight ratios of sorbitol to xylitol were prepared. For comparative purposes, as detailed below, batches of melt crystallized sorbitol (Comparative Experiment A) and of melt crystallized xylitol (Comparative Experiment B) were similarly prepared.

The molten sorbitol starting material, was produced by melting aqueous crystallized sorbitol having a water content of about 0.2% by weight and was maintained at 210° F. prior to introduction into the mixer. The molten xylitol starting material was produced by melting commercially available aqueous crystallized xylitol and maintaining such material at 225° F. in order to keep the moisture content of such molten xylitol to less than about 0.5 weight percent.

The heated starting materials were added to the mixer (in the amounts specified in Table 1 below) and agitated at 20 revolutions per minute for 2 minutes while the jacketed mixer was cooled with water at the temperature indicated. At this point, the mixing was stopped to ensure that the melt temperature had cooled to a temperature below the melting point of the seed crystals to be added (i.e., for sorbitol less than 195° F. for xylitol less than 190° F.). At this point, agitation was continued and the seed crystals (of the composition and in the amounts, in parts by weight, indicated in Table I) were added.

Once crystallization was initiated and the mass began thickening, the mass was dumped into foil covered pans and placed in an oven at 100° F. until fully crystallized.

The reaction conditions and materials employed are summarized in Table I.

TABLE I

| Reactants/ Condition | Example or Comparative Experiment | | | | | | |
|---|---|---|---|---|---|---|---|
| | A | 1 | 2 | 3 | 4 | 5 | B |
| Sorbitol | 1000 | 900 | 750 | 500 | 250 | 100 | — |
| Xylitol | — | 100 | 250 | 500 | 750 | 900 | 1000 |
| Seed | | | | | | | |
| Sorbitol | 10 | 10 | 10 | 5 | — | — | — |
| Xylitol | — | — | — | 5 | 10 | 10 | 10 |
| Total | 1010 | 1010 | 1010 | 1010 | 1010 | 1010 | 1010 |
| Weight Jacket Temp (°F.) | 150 | 150 | 140 | 140 | 130 | 130 | 150 |
| Crystallization Time (min) | 7 | 12 | 24 | 60 | 60 | 40 | 10 |
| Mass Appearance* | | | | | | | |
| After 1 hour | H | H | S/P | S | S | H | H |
| After 24 hours | H | H | H | H | H | H | H |

*H = hard
S = soft
S/P = soft/pliable

EXAMPLES 7-10 AND COMPARATIVE EXPERIMENT C-H

Samples of the crystalline materials produced in Examples 1-5 and Comparative Experiments A and B were broken up and ground down using a Waring blender at high speed and screened through a −20/+80 (U.S. Sieve Series) screens configuration, to produce powders which were small enough to pass through a 20 mesh screen but too large to pass through a 80 mesh screen. 298.5 grams of the powders so produced were blended with 1.5 grams of magnesium stearate in a V blender for 3 minutes in those amounts listed in Table II below. One half gram samples of blend were tabletted in a commercially available Stokes B-2 Press using ¼" FFBE punches under 2 tons of pressure. The appearance of the tablets so produced was recorded, and samples of each were tested in a Strong Cobb Arner hardness tester. The results of such testing is also summarized in Table II.

TABLE II

| Example or Comparative Experiment | Melt*** Crystallized Sorbitol Powder | Melt*** Crystallized Xylitol Powder | Melt*** Crystallized Sorbitol/ Xylitol | Ratio** Sorbitol/ Xylitol (wt. %) | Appearance | Strong Cobb Hardness |
|---|---|---|---|---|---|---|
| C | 298.5 | — | — | 100/0 | Smooth | 10 |
| D | — | 298.5(B) | — | 0/100 | Slightly Gritty | 2 |
| 7 | — | — | 298.5(1) | 90/10 | Smooth | 4 |
| 8 | — | — | 298.5(2) | 75/25 | Smooth | 8 |
| 9 | — | — | 298.5(4) | 25/75 | Smooth | 7 |
| 10 | — | — | 298.5(5) | 10/90 | Smooth | 6 |
| E | 268.6(A) | 26.9(B) | — | 90/10 | Smooth | 8 |
| F | 224.9(A) | 74.4(B) | — | 75/15 | Slightly Gritty | 4 |
| G | 64.4(A) | 224.9(B) | — | 25/75 | Gritty | 4 |
| H | 26.9(A) | 268.6(B) | — | 10/90 | Slightly Gritty | 3 |

*Amounts in grams
**Excluding see crystal content
***Number/Letter in parenthesis refers to earlier Example/Comparative Experiment which was source of powdered ingredient.

The above data indicates that the melt cocrystallized material of this invention affords a means of producing smooth tablets having increased amounts of xylitol.

EXAMPLES 11-15 AND COMPARATIVE EXPERIMENTS I AND J

Samples of the crystalline material produced in Examples 1-5 and Comparative Experiments A and B were ground in a Waring blender and passed through a 40 mesh screen. 54 parts by weight of the screened material of each Example or Comparative Experiment was blended with 25 parts gum base: 19.5 parts of a 70% solids solution of sorbitol: 0.5 parts glycerine: and 1.0 part peppermint flavoring.

The blended materials were sheeted out and scored, with the following results being noted.

TABLE III

| Example or Comparative Experiment | Crystalline* Sorbitol | Crystalline* Xylitol | Cocrystallized* Sorbitol/ Xylitol | Sorbitol**/ Xylitol Ratio | Appearance Sheet | Score |
|---|---|---|---|---|---|---|
| I | 54 | — | — | 100/0 | Good | No Sticking |
| 11 | — | — | 54 | 90/10 | Good | No Sticking |
| 12 | — | — | 54 | 75/25 | Good | No Sticking |
| 13 | — | — | 54 | 50/50 | Slightly Sticky | Very Soft |
| 14 | — | — | 54 | 25/75 | Slightly Sticky | Very Soft |
| 15 | — | — | 54 | 10/90 | Slightly Sticky | Very Soft |
| J | — | 54 | — | 0/100 | Very Soft and Sticky | Very Soft and Sticky |

*Parts by weight
**Not including seed crystal

The above data shows that, employing the melt cocrystallized sorbitol/xylitol of this invention, chewing gums having a substantial amount of xylitol can be prepared with a non-sticky, easily scored texture.

What is claimed is:

1. Melt cocrystallized sorbitol/xylitol.
2. Melt cocrystallized sorbitol/xylitol in accordance with claim 1 wherein the weight ratio of sorbitol to xylitol is between about 99:1 and about 1:99.
3. Melt cocrystallized sorbitol/xylitol in accordance with claim 2 wherein the weight ratio of sorbitol to xylitol is between about 50:50 and about 97:3.
4. Melt cocrystallized sorbitol/xylitol in accordance with claim 3 wherein the weight ratio of sorbitol to xylitol is between about 65:35 and about 95:5.
5. An ingestable composition comprising melt cocrystallized sorbitol/xylitol.
6. An ingestable composition in accordance with claim 5 wherein said composition is in the form of a tablet.
7. An ingestable composition in accordance with claim 5 wherein said composition is in the form of a chewing gum.
8. A method of producing melt crystallized sorbitol/xylitol, which method comprises the steps of:
   a) forming a homogeneous molten blend of sorbitol and xylitol;
   b) cooling said homogeneous molten mixture under agitation until a viscous mass is formed; and
   c) cooling said mass slowly until the sorbitol/xylitol blend becomes fully crystallized.

* * * * *